United States Patent

Sauer et al.

[11] Patent Number: 5,164,117
[45] Date of Patent: Nov. 17, 1992

[54] TERNARY SURFACTANT MIXTURES

[75] Inventors: Joe D. Sauer; Kim R. Smith; James E. Borland; Terry Crutcher, all of Baton Rouge, La.

[73] Assignee: Ethyl Corporation, Richmond, Va.

[21] Appl. No.: 787,616

[22] Filed: Nov. 4, 1991

Related U.S. Application Data

[63] Continuation-in-part of Ser. No. 698,539, May 10, 1991, abandoned.

[51] Int. Cl.$^5$ .................. B01F 17/00; B01F 17/16; B01F 17/28
[52] U.S. Cl. .................. 252/355; 252/550; 252/554; 252/547; 252/DIG. 13; 252/DIG. 14
[58] Field of Search ............ 252/355, 353, 550, 554, 252/547, DIG. 13, DIG. 14

[56] References Cited

U.S. PATENT DOCUMENTS

| | | | |
|---|---|---|---|
| 4,256,611 | 3/1981 | Egan et al. | 252/548 |
| 4,264,479 | 4/1981 | Flanagan | 252/524 |
| 4,416,793 | 11/1983 | Barrat et al. | 252/117 |
| 4,472,297 | 9/1984 | Bolich, Jr. et al. | 252/531 |
| 4,588,514 | 5/1986 | Jones et al. | 252/98 |
| 4,654,158 | 3/1987 | Shepherd, Jr. | 252/91 |
| 4,938,953 | 7/1990 | Pena e al. | 424/70 |
| 5,062,973 | 11/1991 | Kellett | 252/8.25 |
| 5,075,501 | 12/1991 | Borland et al. | 564/297 |

Primary Examiner—Richard D. Lovering
Assistant Examiner—N. Bhat
Attorney, Agent, or Firm—Patricia J. Hogan

[57] ABSTRACT

Surfactant mixtures which have performance and/or cost advantages over the individual components consist of 5–90% by weight of an amine oxide corresponding to the formula RR'R"NO in which R is a primary alkyl group containing 6–24 carbons and R' and R" are independently selected from methyl, ethyl, and 2-hydroxyethyl, 5–90% by weight of a fatty acid alkanolamide, and 5–90% by weight of an alkyl sulfate surfactant. Preferred mixtures are those in which the amine oxide is N-tetradecyldimethylamine oxide, the alkanolamide is cocodiethanolsuperamide, and the alkyl sulfate is sodium lauryl sulfate.

5 Claims, No Drawings

TERNARY SURFACTANT MIXTURES

CROSS-REFERENCE TO RELATED APPLICATION

This application is a continuation-in-part of copending application Ser. No. 698,539, filed May 10, 1991, now abandoned.

FIELD OF INVENTION

This invention relates to surfactant compositions and more particularly to such compositions which are mixtures of amine oxides, alkanolamides, and alkyl sulfates.

BACKGROUND

It is known that various surfactants have been found to be useful in cleaning compositions, such as shower gels, shampoos, and light duty detergents (e.g., dish detergents)—compositions in which good foamability is a prerequisite for consumer approval. The surfactants which have been used to the greatest extent in such compositions are anionic surfactants, such as alkyl sulfates, alkyl ether sulfates, sulfonates, sulfosuccinates, and sarcosinates.

Although the use of anionic surfactants in these compositions permits the attainment of desirable characteristics, including good foamability, it would be beneficial to find other surfactants which could provide equal or better performance at a lower cost. However, other known surfactants, such as amine oxides, betaines, and alkanolamides, are either more costly than the anionic surfactants or give poorer performance, e.g., smaller foam volume, when substituted for the anionic surfactants.

It is sometimes advantageous to use mixtures of surfactants in cleaning compositions when the surfactants can serve different functions, e.g., one serving to improve foamability and another serving to adjust viscosity. However, known surfactant mixtures typically provide a compromise between what can be achieved with the surfactant ingredients alone. Thus, e.g., a mixture of (A) a more costly surfactant which provides good foamability or viscosity by itself with (B) a less expensive surfactant which provides poorer foamability or viscosity by itself will provide an intermediate foamability or viscosity.

SUMMARY OF INVENTION

It has been found that a mixture of 5-90% by weight of an amine oxide corresponding to the formula RR'R"NO in which R is a primary alkyl group containing 6-24 carbons and R' and R" are independently selected from methyl, ethyl, and 2-hydroxyethyl, 5-90% by weight of a fatty acid alkanolamide, and 5-90% by weight of an alkyl sulfate surfactant provides performance and/or cost advantages over the individual components of the surfactant mixture.

DETAILED DESCRIPTION

Amine oxides which can be used in the practice of the invention are compounds corresponding to the formula RR'R"NO in which R is a primary alkyl group containing 6-24 carbons, preferably 10-18 carbons, and R' and R" are independently selected from methyl, ethyl, and 2-hydroxyethyl. The preferred amine oxides are those in which the primary alkyl group has a straight chain in at least most of the molecules, generally at least 70%, preferably at least 90% of the molecules; and the amine oxides which are especially preferred are those in which R contains 10-18 carbons and R' and R" are both methyl.

Exemplary of the preferred amine oxides are the N-hexyl-, N-octyl-, N-decyl-, N-dodecyl-, N-tetradecyl-, N-hexadecyl-, N-octadecyl-, N-eicosyl-, N-docosyl-, and N-tetracosyldimethylamine oxides, the corresponding amine oxides in which one or both of the methyl groups are replaced with ethyl or 2-hydroxyethyl groups, etc., and mixtures thereof. A particularly preferred amine oxide is N-tetradecyldimethylamine oxide.

Fatty acid alkanolamides which may be used in admixture with the amine oxides and alkyl sulfates are the known nonionic surfactants usually designated as superamides, i.e., alkanolamides obtained by reacting a fatty acid, usually a fatty acid containing 8-18 carbons, with an alkanolamine in equimolar proportions. The preferred alkanolamide is cocodiethanolsuperamide.

The alkyl sulfate utilized in the mixture may be any of the alkyl sulfates conventionally employed as surfactants. Such anionic surfactants are usually alkali metal or ammonium salts of alkyl sulfates in which the alkyl groups contain 8-18 carbons, and sodium lauryl sulfate is generally preferred.

Different proportionations of the ingredients of the surfactant mixtures provide different advantages. Thus, when improved foamability at a lower cost is the primary goal, the mixtures should contain about 5-50%, preferably about 10-35% by weight of the amine oxide; about 5-70%, preferably about 5-35% by weight of the alkanolamide; and about 25-90%, preferably about 30-75% by weight of the alkyl sulfate. When improved viscosity is particularly desired, on the other hand, the mixtures should contain about 5-90% by weight of the amine oxide; about 5-90% by weight of the alkanolamide; and about 5-25%, preferably about 5-15% by weight of the alkyl sulfate; and it is preferred for the alkanolamide/alkyl sulfate weight ratio in the mixtures to be at least about 1/1, most preferably at least about 2/1.

The surfactant mixtures which are most cost-effective in producing foam are those containing about 12% by weight of the amine oxide, about 13% by weight of the alkanolamide, and about 75% by weight of the alkyl sulfate, while those which are most cost-effective in achieving high viscosity are those containing about 12% by weight of the amine oxide, about 75% by weight of the alkanolamide, and about 13% by weight of the alkyl sulfate.

Although the surfactant mixtures which provide higher viscosities are also beneficial, those which provide acceptable levels of foam more economically than the individual components of the mixtures are usually the most advantageous to prepare. This characteristic of the mixtures makes them valuable for use in the cleaning compositions which require foaming for customer approval, e.g., shampoos, shower gels, and light duty detergents.

When employed in such compositions, the surfactant mixtures are utilized in an aqueous medium, which typically constitutes about 10-90% of the weight of the compositions; and they may be used in conjunction with other ingredients of the types conventionally used in the compositions. Such ingredients include, e.g., viscosity improvers, pH adjusters, colorants, pearlizing agents, clarifying agents, fragrances, preservatives, antioxidants, chelating agents, skin and hair conditioners, botanical extracts, and antibacterial agents.

The following examples are given to illustrate the invention and are not intended as a limitation thereof. Unless otherwise specified, quantities mentioned in the examples are quantities by weight.

EXAMPLE I

Prepare several aqueous surfactant solutions having a total surfactant content of 5% from N-tetradecyldimethylamine oxide (AX), cocodiethanolsuperamide (SA), and sodium lauryl sulfate (AS). The proportions of these surfactants used in preparing each of the solutions, as well as the viscosities of the solutions, are shown in Table I.

TABLE I

| % AX | % SA | % AS | Viscosity (mPa · s) |
|------|------|------|---------------------|
| 100  | 0    | 0    | 23                  |
| 0    | 100  | 0    | 37                  |
| 0    | 0    | 100  | 2                   |
| 12   | 75   | 13   | 1040                |
| 75   | 12   | 13   | 1000                |
| 25   | 50   | 25   | 624                 |
| 34   | 33   | 33   | 102                 |
| 50   | 25   | 25   | 2                   |
| 12   | 13   | 75   | 2                   |
| 25   | 25   | 50   | 2                   |

EXAMPLE II

Dissolve varying amounts of N-tetradecyldimethylamine oxide (AX), cocodiethanolsuperamide (SA), and sodium lauryl sulfate (AS) in hard water (200 ppm as $CaCO_3$) to provide solutions having a total surfactant content of 0.1%. Measure the foamability of the surfactants by (1) placing 30 mL of each of the solutions in a 100 mL stoppered graduated cylinder, (2) inverting the cylinder ten times, (3) measuring the foam height, (4) repeating steps 1–3 twice, and (5) calculating the average of the three measurements. The proportions of amine oxide, alkanolamide, and alkyl sulfate used in preparing each of the solutions and the foam heights obtained from them are shown in Table II.

TABLE II

| % AX | % SA | % AS | Foam Height (mL) |
|------|------|------|------------------|
| 100  | 0    | 0    | 33               |
| 0    | 100  | 0    | 17               |
| 0    | 0    | 100  | 30               |
| 12   | 13   | 75   | 42               |
| 25   | 25   | 50   | 33               |
| 34   | 33   | 33   | 37               |
| 50   | 25   | 25   | 33               |
| 25   | 50   | 25   | 34               |
| 75   | 12   | 13   | 18               |
| 12   | 75   | 13   | 28               |

What is claimed is:

1. A surfactant mixture consisting of 5–90% by weight of an amine oxide corresponding to the formula RR'R''NO in which R is a primary alkyl group containing 6–24 carbons and R' and R'' are independently selected from the group consisting of methyl, ethyl, and 2-hydroxyethyl, 5–15% by weight of a fatty acid alkanolamide, and 5–90% by weight of an alkyl sulfate surfactant.

2. The surfactant mixture of claim 1 wherein R is a primary alkyl group containing 10–18 carbons, R' and R'' are methyl, and the alkanolamide and alkyl sulfate contain alkyl groups of 8–18 carbons.

3. The surfactant mixture of claim 2 wherein the amine oxide is N-tetradecyldimethylamine oxide, the alkanolamide is cocodiethanolsuperamide, and the alkyl sulfate is sodium lauryl sulfate.

4. The surfactant mixture of claim 1 wherein the alkanolamide/alkyl sulfate weight ratio is at least about 1/1.

5. The surfactant mixture of claim 4 wherein the alkanolamide/alkyl sulfate weight ratio is at least about 2/1.

* * * * *